(12) United States Patent
Bruneau et al.

(10) Patent No.: US 7,780,709 B2
(45) Date of Patent: Aug. 24, 2010

(54) IMPLANTS AND METHODS FOR INTER-TRANSVERSE PROCESS DYNAMIC STABILIZATION OF A SPINAL MOTION SEGMENT

(75) Inventors: Aurelien Bruneau, Memphis, TN (US); Tommy Carls, Memphis, TN (US); Eric C. Lange, Collierville, TN (US); Fred J. Molz, IV, Collierville, TN (US); Matthew M. Morrison, Cordova, TN (US); Jonathan Dewey, Memphis, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 261 days.

(21) Appl. No.: 11/104,267

(22) Filed: Apr. 12, 2005

(65) Prior Publication Data

US 2006/0241613 A1    Oct. 26, 2006

(51) Int. Cl.
*A61B 17/70* (2006.01)
(52) U.S. Cl. ................... 606/279; 606/246
(58) Field of Classification Search ... 623/16.11–17.16; 606/61, 246, 248, 249, 279
See application file for complete search history.

(56) References Cited

U.S. PATENT DOCUMENTS

| | | | |
|---|---|---|---|
| 2,677,369 A | 5/1954 | Knowles | |
| 2,774,350 A | 12/1956 | Cleveland, Jr. | |
| 3,648,691 A | 3/1972 | Lumb et al. | |
| 3,693,616 A | 9/1972 | Roaf et al. | |
| 4,011,602 A | 3/1977 | Rybicki et al. | |
| 4,257,409 A | 3/1981 | Bacal et al. | |
| 4,269,178 A | 5/1981 | Keene | |
| 4,422,451 A | 12/1983 | Kalamchi | |
| 4,554,914 A | 11/1985 | Kapp et al. | |
| 4,573,454 A | 3/1986 | Hoffman | |
| 4,604,995 A | 8/1986 | Stephens et al. | |
| 4,686,970 A | 8/1987 | Dove et al. | |
| 4,827,918 A | 5/1989 | Olerud | |
| 4,913,134 A | 4/1990 | Luque | |
| 5,010,879 A * | 4/1991 | Moriya et al. ................. 606/61 |

(Continued)

FOREIGN PATENT DOCUMENTS

DE    28 21 678 A1    11/1979

(Continued)

OTHER PUBLICATIONS

Posterior Spinal Instrumentation for Thoracolumbar Tumor and Trauma Reconstruction, Seminars in Spine Surgery, vol. 9, No. 3, Sep. 1997, pp. 260-277.

(Continued)

*Primary Examiner*—Eduardo C Robert
*Assistant Examiner*—Tara R George
(74) *Attorney, Agent, or Firm*—Coats and Bennett, P.L.L.C.

(57) ABSTRACT

An implant assembly for stabilizing a spinal motion segment includes a flexible spacer member positionable between adjacent transverse processes to dynamically limit movement of the upper and lower transverse processes toward one another upon extension of the spinal motion segment. The implant assembly may also include an engaging member positionable about one or more posterior elements of a spinal motion segment to secure the spacer member thereto.

6 Claims, 3 Drawing Sheets

U.S. PATENT DOCUMENTS

| | | | |
|---|---|---|---|
| 5,011,484 A | 4/1991 | Breard | |
| 5,047,055 A | 9/1991 | Bao et al. | |
| 5,092,866 A | 3/1992 | Breard et al. | |
| 5,116,334 A | 5/1992 | Cozad et al. | |
| 5,201,734 A | 4/1993 | Cozad et al. | |
| 5,306,275 A | 4/1994 | Bryan | |
| 5,360,430 A | 11/1994 | Lin | |
| 5,366,455 A * | 11/1994 | Dove et al. | 606/61 |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |
| 5,609,592 A | 3/1997 | Brumfield et al. | |
| 5,609,634 A * | 3/1997 | Voydeville | 623/13.11 |
| 5,628,756 A | 5/1997 | Barker, Jr. et al. | |
| 5,645,599 A * | 7/1997 | Samani | 623/17.16 |
| 5,674,295 A | 10/1997 | Ray et al. | |
| 5,676,702 A | 10/1997 | Ratron | |
| 5,690,649 A | 11/1997 | Li | |
| 5,725,582 A | 3/1998 | Bevan et al. | |
| 5,810,815 A | 9/1998 | Morales | |
| 5,810,818 A | 9/1998 | Errico et al. | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,066,140 A | 5/2000 | Gertzbein et al. | |
| 6,068,630 A | 5/2000 | Zucherman et al. | |
| 6,132,464 A | 10/2000 | Martin | |
| 6,293,949 B1 | 9/2001 | Justis et al. | |
| 6,312,431 B1 | 11/2001 | Asfora | |
| 6,352,537 B1 | 3/2002 | Strnad | |
| 6,364,883 B1 | 4/2002 | Santilli | |
| 6,402,750 B1 | 6/2002 | Atkinson et al. | |
| 6,440,169 B1 | 8/2002 | Elberg et al. | |
| 6,451,019 B1 | 9/2002 | Zucherman et al. | |
| 6,500,178 B2 | 12/2002 | Zucherman et al. | |
| 6,582,433 B2 | 6/2003 | Yun | |
| 6,626,944 B1 * | 9/2003 | Taylor | 623/17.16 |
| 6,645,207 B2 | 11/2003 | Dixon et al. | |
| 6,695,842 B2 | 2/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,752,831 B2 | 6/2004 | Sybert et al. | |
| 6,761,720 B1 | 7/2004 | Senegas | |
| 6,835,205 B2 | 12/2004 | Atkinson et al. | |
| 6,946,000 B2 | 9/2005 | Senegas et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,442,208 B2 * | 10/2008 | Mathieu et al. | 623/17.11 |
| 7,445,637 B2 | 11/2008 | Taylor | |
| 2002/0143331 A1 | 10/2002 | Zucherman et al. | |
| 2003/0040746 A1 | 2/2003 | Mitchell et al. | |
| 2003/0065330 A1 | 4/2003 | Zucherman et al. | |
| 2003/0153915 A1 | 8/2003 | Nekozuka et al. | |
| 2003/0216736 A1 | 11/2003 | Robinson et al. | |
| 2004/0097931 A1 | 5/2004 | Mitchell | |
| 2004/0106995 A1 | 6/2004 | Le Couedic et al. | |
| 2004/0181282 A1 | 9/2004 | Zucherman et al. | |
| 2004/0243239 A1 * | 12/2004 | Taylor | 623/17.13 |
| 2005/0010293 A1 | 1/2005 | Zucherman et al. | |
| 2005/0049708 A1 | 3/2005 | Atkinson et al. | |
| 2005/0055031 A1 | 3/2005 | Lim | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0261768 A1 | 11/2005 | Trieu | |
| 2005/0288672 A1 | 12/2005 | Feree | |
| 2006/0004447 A1 | 1/2006 | Mastrorio et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0136060 A1 | 6/2006 | Taylor | |
| 2006/0149242 A1 | 7/2006 | Kraus et al. | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0264938 A1 | 11/2006 | Zucherman et al. | |
| 2006/0271044 A1 | 11/2006 | Petrini et al. | |
| 2006/0293662 A1 | 12/2006 | Boyer, II et al. | |
| 2007/0112350 A1 | 5/2007 | Deneuvillers et al. | |

FOREIGN PATENT DOCUMENTS

| | | |
|---|---|---|
| DE | 2821678 A1 | 11/1979 |
| EP | 0322334 B1 | 2/1992 |
| EP | 1138268 A1 | 10/2001 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2816197 A1 | 11/2000 |
| FR | 2816197 A1 | 5/2002 |
| GB | 780652 | 8/1957 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | 2005037150 A1 | 4/2005 |
| WO | WO 2005/044118 A1 | 5/2005 |
| WO | WO 2005/110258 A1 | 11/2005 |
| WO | WO 2007/034516 A1 | 3/2007 |

OTHER PUBLICATIONS

Reduction and Fixation of Late Diagnosed Lower Cervical Spine Dislocations Using the Daab Plate, Archives of Orthopaedic and Traumatic Surgery, 1984, pp. 353-355.

Posterior Spinal Fusion Using Internal Fixation with the Daab Plate, Act. Orthop. Scand. 55, pp. 310-314, 1984.

The Value of the WIlson Plate in Spinal Fusion, M.C. Cobey, M.D., May 1971.

Medtronic Sofamor Danek, "CD Horizon Legacy 5.5, Spinal System—Deformity Surgical Technique", 2004, pp. 1-51, Medtronic Sofamor Danek USA, Inc., Memphis, TN.

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insaility, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90°Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

* cited by examiner

IMPLANTS AND METHODS FOR INTER-TRANSVERSE PROCESS DYNAMIC STABILIZATION OF A SPINAL MOTION SEGMENT

BACKGROUND

Implants can be positioned between adjacent spinous processes to provide resistance to vertebral movement as a result of extension of the spinal column. These implants can provide a shock absorber or bumper that dynamically limits spinal extension. The implants can be secured to the adjacent spinous processes with looped cables or straps that extend completely about the spinous processes and implant to maintain positioning of the implant between the spinous processes while also limiting spinal flexion. While spinous process implants provide dynamic stabilization along the spinal midline, dynamic stabilization at uni-lateral or bi-lateral locations of the posterior vertebral elements is not achieved with such implants.

SUMMARY

There is provided spinal implants, implant assemblies and implants that provide uni-lateral or bi-lateral dynamic stabilization of a spinal motion segment through the posterior vertebral elements.

According to one aspect, a spinal implant includes a spacer member extending between opposite upper and lower ends. The upper and lower ends each include a pair of arms and a recessed surface between the pair of arms. The arms are structured to receive a respective adjacent one of upper and lower transverse processes of a spinal motion segment. The spacer member includes a compressible body sized and shaped to extend between the upper and lower transverse processes to dynamically limit movement of the upper and lower transverse processes toward one another upon extension of the spinal motion segment.

According to another aspect, a spinal implant system includes a first spacer member extending between opposite upper and lower ends structured to receive a respective adjacent one of upper and lower transverse processes of a spinal motion segment at a first side of the spinal midline. The system further includes a second spacer member extending between opposite upper and lower ends structured to receive a respective adjacent one of upper and lower transverse processes of a spinal motion segment at a second side of the spinal midline. Each of the spacer members includes a compressible body sized and shaped to extend between the upper and lower transverse processes to dynamically limit movement of the upper and lower transverse processes toward one another upon extension of the spinal motion segment.

According to a further aspect, a method for stabilizing a spinal motion segment comprises: positioning a spacer member between adjacent upper and lower transverse processes of the spinal motion segment, the spacer member including an upper end contacting an inferior surface of the upper transverse process and a lower end contacting a superior surface of the lower transverse process; and dynamically stabilizing the spinal motion segment with the spacer member resiliently compressing between the transverse processes in response to extension of the spinal motion segment.

These and other aspects will be discussed further below.

DESCRIPTION OF THE ILLUSTRATED EMBODIMENTS

Figure 1:
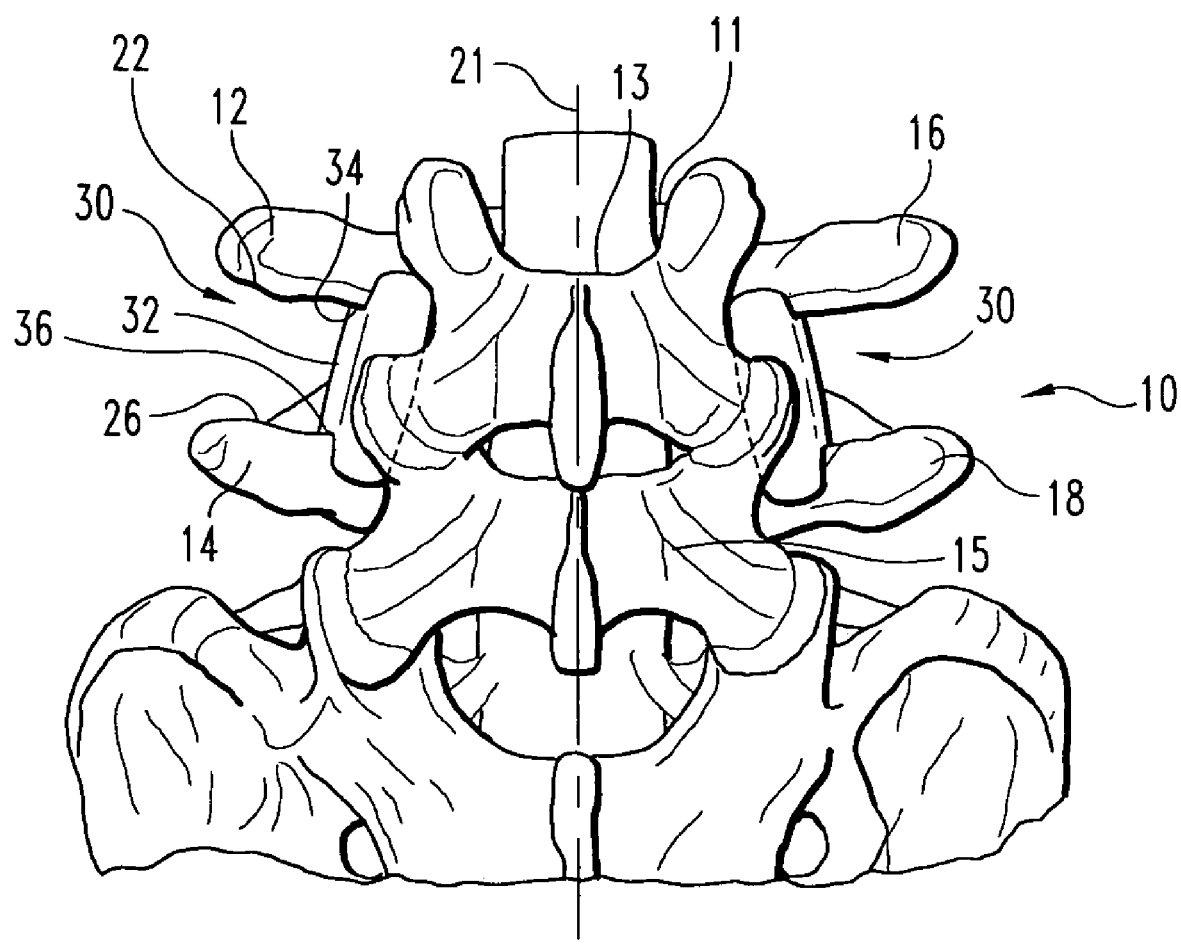
FIG. 1 is an elevation view of a posterior portion of a spinal column motion segment with implant assemblies engaged thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Implants are positionable between adjacent transverse processes of a spinal motion segment to dynamically stabilize and limit spinal extension and/or flexion. The implant includes a spacer member received between the transverse processes that is compressible to allow extension motion of the motion segment while maintaining a distraction force between the transverse processes.

In one implant system, spacer members are positioned bi-laterally relative to a spinal motion segment in order to provide bi-lateral stabilization. In another implant system, uni-lateral stabilization is provided by the implant system. In still other systems, multi-level vertebral stabilization is contemplated for either uni-lateral or bi-lateral systems. The implant systems may be employed either alone or in combination with other implants, such as rods, plates, tethers, interbody fusion devices, interbody spacers, artificial discs, annulus repair systems, or staples, for example.

In a further form, one or more engaging members in the form of a tether couples the implant to one or more posterior vertebral elements or implants. The engaging members can be engaged to the spacer member, or extend through the spacer member. The engaging members can be engaged to the posterior elements in a configuration that limits spinal flexion. Alternatively or additionally, the engaging members can be engaged to the posterior elements in a manner that prevents the spacer member from being displaced from its implantation location between the transverse processes.

In FIG. 1 there is shown a spinal column segment 10 including an upper vertebra 11, a lower vertebra 15 and a spinal disc 13 therebetween along a central axis 21 of the spinal column. The vertebrae 11, 15 and disc 13 comprise a spinal motion segment, it being understood that a spinal motion segment may include multiple vertebral levels. Upper vertebra 11 includes a first upper transverse process 12 and a second upper transverse process 16. Lower vertebra 15 includes a first lower transverse process 14 and a second lower transverse process 18. The transverse processes 12, 14, 16, 18 comprise posterior elements of the vertebrae of the spinal motion segment along with the spinous processes 17, 19, facets, pedicles and other posterior structures of each vertebrae 11, 15.

A spinal implant 30 is positioned in engagement with the posterior vertebral elements to provide dynamic spinal stabilization. Spinal implant 30 includes a spacer member 32 extending between and contacting adjacent surfaces of transverse processes 12, 14 to limit movement of the spinous processes toward one another as a result of extension of the spinal motion segment. For example, spacer member 32 can include an upper end 34 in contact with inferior surface 22 of transverse process 12, and a lower end 36 in contact with superior surface 26 of transverse process 14. Spacer member 32 can include a body structured to resiliently compress in response to extension of the spinal column, providing resistance to the extension forces and limiting movement of the transverse processes 12, 14 toward one another as spacer member 32 is compressed.

FIG. 1 further shows a second spinal implant 30 on the other side of central axis 21 of the spinal column. The second spacer member 32 can be structured like the other implant 30, and is configured to extend between and contact adjacent surfaces of transverse processes 16, 18 to limit movement of the spinous processes toward one another as a result of extension of the spinal motion segment. The implants 30 work bi-laterally to provide bi-lateral stabilization of spinal column segment 10. Additional implants 30 may be provided at one or more additional vertebral levels for multi-level stabilization procedures. It is further contemplated that implants 30 may be employed to uni-laterally stabilize one or more vertebral levels. The spinal implants, either alone or in combination, can function to distract the spinal space and/or the spinal foramen to relieve nerve root pressure and decompress spinal elements. The implants provide overall stability while maintaining motion capabilities of the spinal motion segment.

Figure 2:
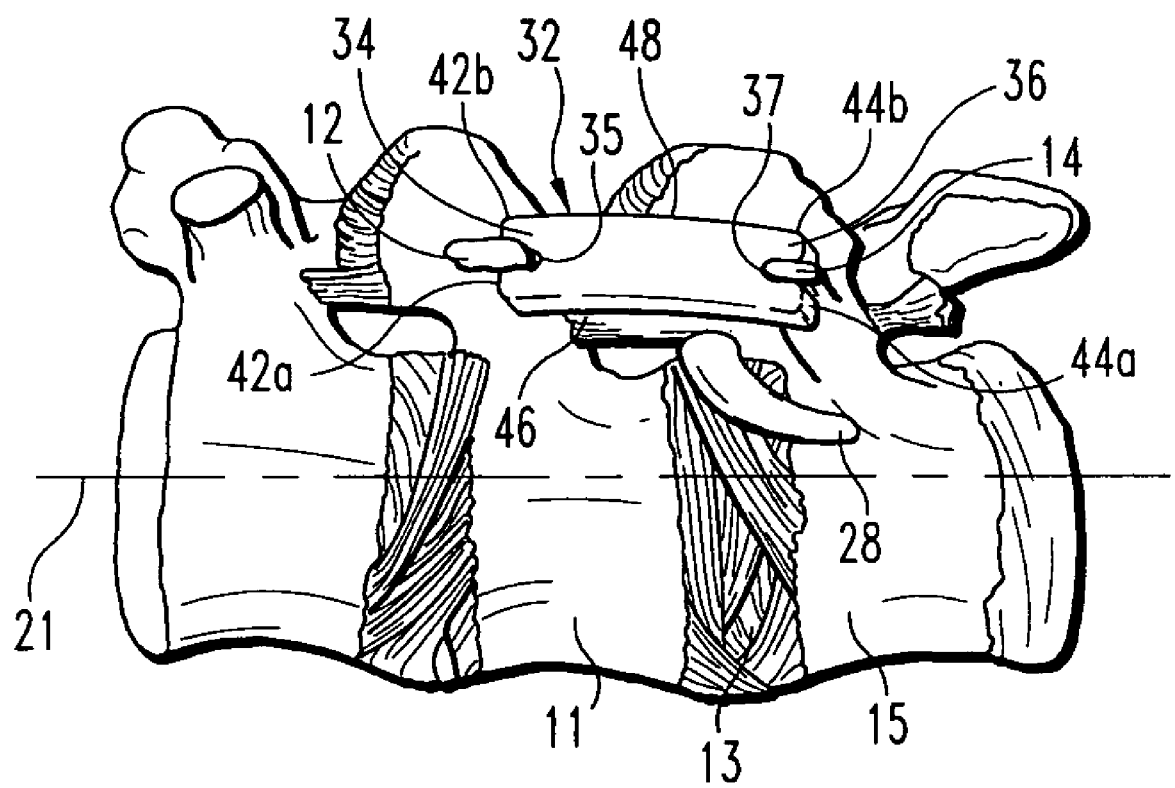
FIG. 2 is a lateral view of the spinal column motion segment of FIG. 1.

As further shown in FIG. 2, spacer member 32 includes a pair of upper arms 42 and a pair of lower arms 44. Upper arms 42 define a concavely curved upper surface 35 therebetween, and lower arms 44 define a concavely curved lower surface 37 therebetween. The concavely curved surfaces 35, 37 can conform generally to or be conformable to the surface of the transverse process against which the surface is positioned. Arms 42, 44 extend along opposite sides of and receive the respective transverse process 12, 14 to resist dislodgement of spacer member 32 from its positioning between transverse processes 12, 14.

In its implanted orientation, spacer member 32 includes an anteriorly oriented surface 46 and a posteriorly oriented surface 48. Anteriorly oriented surface 46 can include a concave curvature to fit over the exiting nerve root 28 and prevent or avoid any impingement thereof. Posteriorly oriented surface 48 can be convexly curved as illustrated, or can include a concave curvature, or it can be linear in form.

In addition, each of the arm pairs 42, 44 includes a posterior arm 42a, 44a and an anterior arm 42b, 44b. In the illustrated embodiment, posterior arms 42a, 44a have a thickness that is less than the thickness of the anterior arms 42b, 44b. The reduced thickness limits the amount of spacer material in the area where nerve root 28 exits the spinal foramen, increasing the space available for nerve root 28 to pass.

Figure 3:
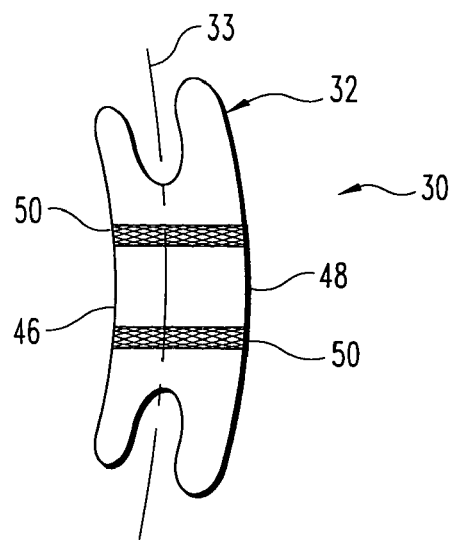
FIG. 3 is an elevation view of another embodiment implant assembly.

In a further embodiment, it is contemplated that stiffening members can be provided to enhance or increase the stiffness of spacer member 32. For example, as shown in FIG. 3, a stiffening member 50 is shown in the form of a band that extends about and contacts the perimeter of spacer member 32 in a direction transverse to central axis 33. Multiple stiffening members 50 can be provided about spacer member 32 to allow the stiffness profile of spacer member 32 to be increased or decreased by adding or removing stiffening members 50. In another embodiment, stiffening member 50 includes a width that extends along a substantial portion of the length of spacer member 32.

Figure 4:
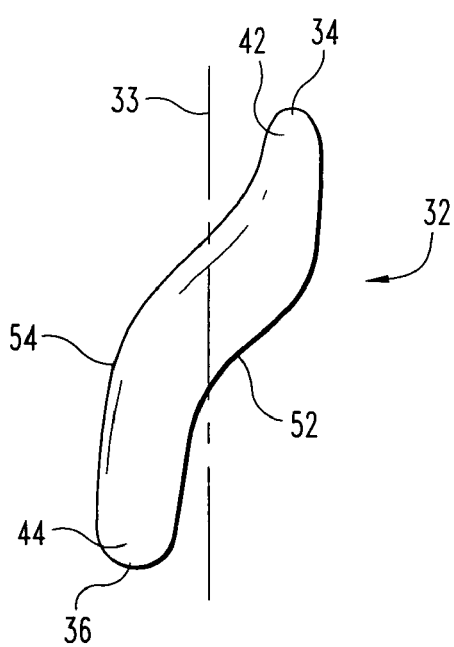
FIG. 4 is an elevation view of another embodiment implant assembly.

In FIG. 3 there is shown one embodiment shape for spacer member 32 in the medial-lateral direction when in its implantation orientation. FIG. 4 shows one embodiment of spacer member 32 positionable along the left hand side of the spinal column and in an elevation view looking from the posterior to anterior direction. Spacer member 32 extends between upper end 34 and lower end 36, and arms 42 are provided at upper end 34 and arms 44 are provided at lower end 36 as discussed above. A central axis 33 divides spacer member 32 into a right hand or medial side and a left hand or lateral side. Spacer member 32 includes a medial surface 52 extending along the medial side and a lateral surface 54 extending along the lateral side. Adjacent lower end 36, medial surface 52 is offset laterally toward or to one side of central axis 33 along lower arms 44. Medial surface 52 extends transversely to central axis 33 from lower arms 44 to upper arms 42 at upper end 34. Along upper arms 42, medial surface 52 is offset medially of central axis 33 and also offset medially with respect to the portion of medial surface 52 along lower arms 44.

The offsetting medial surface 52 is shaped to facilitate placement of spacer member 32 along or against the bony structure and shapes at the junctions of the transverse process and pedicle. By allowing placement of spacer member 32 as close as possible to the junction of the transverse process with the pedicle, the moment arm on the transverse process is minimized. In another embodiment, spacer member 32 is made with material properties that deform to allow conformance upon contact of spacer member 32 with the bony structure. In still other embodiments, the medial and lateral surfaces can be parallel to one another.

Figure 5:
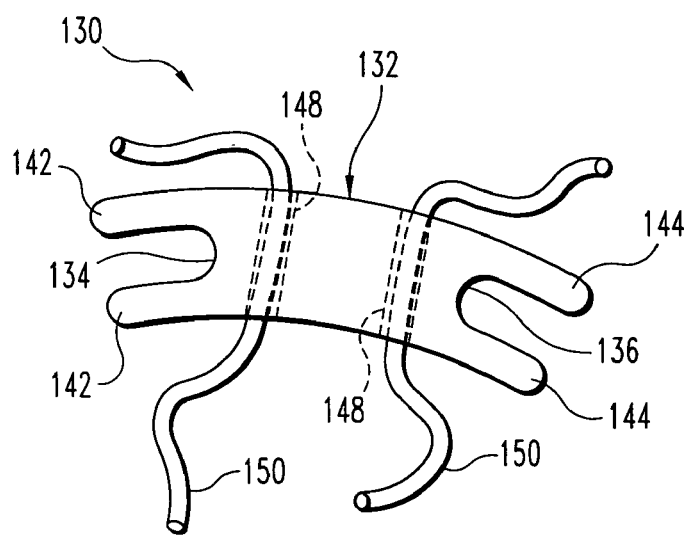
FIG. 5 is an elevation view of another embodiment implant assembly.

Referring now to FIG. 5, there is shown an implant assembly 130. Implant assembly 130 includes a spacer member 132 having a body extending between an upper end 134 and a lower end 136. A first pair of arms 142 are provided adjacent upper end 134, and a second pair of arms 144 are provided adjacent lower end 136. Spacer member 132 is similar to spacer member 32 discussed above and is structured for positioning between and receiving adjacent upper and lower transverse processes of a spinal motion segment. However, implant assembly 130 includes an engaging member 150 extending therefrom to attach spacer member 132 to posterior vertebral elements or implants of the spinal motion segment.

Spacer member 132 includes through-passages 148 extending between opposite sides thereof, which include the anterior and posterior sides of spacer member 132 in the illustrated embodiment. Passages 148 receive engaging member 150 therethrough. Engaging member 150 may comprise multiple engaging members, or a single engaging member looped through passages 148. Still other embodiments contemplate a single passage 148, or three or more passages 148, through which one or more engaging members 150 are positioned.

Engaging member 150 can be in the form of a tether, cord, wire, cable, suture, band, strap, belt, or other suitable structure for manipulation and securement to one or more posterior vertebral elements. Engaging member 150 may be wrapped or positioned around posterior vertebral elements and then maintained in position with a crimp or other suitable fastener. Furthermore, engaging member 150 can be coupled to spacer member 132 in any suitable manner. In one embodiment, engaging member 150 is movably coupled to spacer member 132. Engaging member 150 can be integrally formed with spacer member 132, or can be attached by a fastener, suture, anchor, cable, link, over-molding or other suitable connection. Spacer member 132 can be provided with ears, eyelets, recesses or other suitable structure to facilitate engagement of engaging member 150 to spacer member 132. Engaging member 150 may be employed in spinal stabilization procedures where it is desired to limit spinal flexion by, for example, wrapping engaging member 150 about the superior surface of the upper transverse process and the inferior surface of the lower transverse process. Engaging member 150 may alternatively be employed as a retention mechanism to maintain spacer member 132 in position between the transverse processes.

With respect to the various embodiments described herein, the engaging member can be joined or fixed to the spacer member using various devices and/or techniques, or can be integrally formed with or form an extension of the spacer member. The spacer member can be joined or attached to the engaging member by, for example, sewing the engaging member to the spacer member, thermal welding or bonding, adhesive bonding, three dimensional weaving or braiding, screws, staples, pins, tacks or rivet fixation. Furthermore, the engaging member can be secured to the spacer member either before or after the spacer member is placed between the transverse processes. The engaging member can be engaged to other engaging members of other implant assemblies or to other implants engaged to the spinal column in the surgical procedure.

The spacer member can be fabricated from components that are flexible or exhibit at least some flexibility. Examples of such components include woven fabric tubing, woven and non-woven mesh, or braided or woven structures, sutures, tethers, cords, planar members, bands, wires, cables, or any other component capable of extending between and supporting the adjacent transverse processes. Additionally, the spacer member may be resilient and/or elastic so it can assume various shapes during and after insertion and attachment.

The spacer member can be made from any biocompatible material, material of synthetic or natural origin, and material of a resorbable or non-resorbable nature. Suitable examples of spacer member material include autograft, allograft or xenograft; tissue materials including soft tissues, connective tissues, demineralized bone matrix and combinations thereof; resorbable materials including polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, poly-paraphenylene terephthalamide, polyetheretherketone, cellulose, and combinations thereof.

The engaging members described herein can be made from any one or combinations of biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are carbon-reinforced polymer composites, shape-memory alloys, titanium, titanium alloys, cobalt chrome alloys, stainless steel, and combinations thereof.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for stabilizing a spinal motion segment, comprising:
    positioning a spacer between adjacent upper and lower transverse processes of the spinal motion segment, the spacer including:
        a compressible spacer body having opposite upper and lower ends;
        said upper end having a first pair of arms and a first recessed surface disposed therebetween forming a concave upper saddle that contacts an inferior surface of the upper transverse process;
        said lower end having a second pair of arms and a second recessed surface disposed therebetween forming a concave lower saddle that contacts a superior surface of the lower transverse process;
    wherein the disposing comprises disposing the spacer such that:
        a sagittal reference plane extends transverse to the upper and lower saddles and the upper and lower transverse processes with a central axis of the spacer body disposed in the sagittal reference plane;
        wherein, when viewed in from a posterior direction along the sagittal plane, the upper and lower saddles are disposed on opposite sides of the central axis so as be non-overlappingly laterally offset;
    thereafter, dynamically stabilizing the spinal motion segment with the spacer resiliently compressing between the transverse processes in response to extension of the spinal motion segment.

2. The method of claim 1 further comprising engaging the spacer to posterior vertebral elements of the spinal motion segment with a tether.

3. The method of claim 1 further comprising increasing a stiffness of the spacer body by disposing a stiffening member about the body of the spacer body so as to contact a perimeter of the spacer body between the upper and lower ends while in a transverse orientation to the central axis of the body.

4. The method of claim 1 wherein the positioning the spacer between adjacent upper and lower transverse processes comprises positioning a spacer between adjacent upper and lower transverse processes in spaced relation to the spinal foramen; wherein the spacer body includes a concavely curving anterior surface to aid in the positioning in spaced relation.

5. The method of claim 1 wherein said spacer is a first spacer and further comprising:
    positioning a second spacer between adjacent upper and lower transverse processes of the spinal motion segment at a side of the spinal midline opposite the first spacer the second spacer including an upper end contacting an inferior surface of the corresponding upper transverse process and a lower end contacting a superior surface of the corresponding lower transverse process; and
    dynamically stabilizing the spinal motion segment with the second spacer resiliently compressing between the corresponding transverse processes in response to extension of the spinal motion segment.

6. The method of claim 5, wherein positioning the spacer members provides bilateral dynamic stabilization of a spinal motion segment.

* * * * *